(12) United States Patent
Ferguson et al.

(10) Patent No.: US 8,762,766 B2
(45) Date of Patent: *Jun. 24, 2014

(54) DISTRIBUTED FAULT TOLERANT ARCHITECTURE FOR A HEALTHCARE COMMUNICATION SYSTEM

(71) Applicant: Hill-Rom Services, Inc., Batesville, IN (US)

(72) Inventors: David C. Ferguson, Wake Forest, NC (US); Richard J. Schuman, Cary, NC (US); Danny C. Woodward, II, Daytona Beach, FL (US); Karl E. Harper, Durham, NC (US); Patricia A. Glidewell, Cary, NC (US); Ralph J. Weaver, Cary, NC (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/771,718

(22) Filed: Feb. 20, 2013

(65) Prior Publication Data

US 2013/0159423 A1 Jun. 20, 2013

Related U.S. Application Data

(63) Continuation of application No. 13/241,461, filed on Sep. 23, 2011, now Pat. No. 8,392,747, which is a continuation of application No. 12/369,818, filed on Feb. 12, 2009, now Pat. No. 8,046,625.

(60) Provisional application No. 61/066,877, filed on Feb. 22, 2008, provisional application No. 61/066,882, filed on Feb. 22, 2008, provisional application No. 61/066,883, filed on Feb. 22, 2008, provisional application No. 61/066,918, filed on Feb. 22, 2008, provisional application No. 61/145,306, filed on Jan. 16, 2009.

(51) Int. Cl.
*G06F 11/00* (2006.01)

(52) U.S. Cl.
USPC .............................................. 714/1

(58) Field of Classification Search
USPC .............................................. 714/1
See application file for complete search history.

(56) References Cited

U.S. PATENT DOCUMENTS 2,330,356 A 9/1943 Belliveau
2,335,524 A 11/1943 Lomax (Continued)

FOREIGN PATENT DOCUMENTS

EP 1 623 666 A2 2/2006
GB 250 769 4/1926

(Continued)

OTHER PUBLICATIONS

Hill-Rom A Hillenbrand Industry, The COMposer® System Installation Manual, 2003.

(Continued)

*Primary Examiner* — Bryce Bonzo
(74) *Attorney, Agent, or Firm* — Barnes & Thornburg LLP (57) ABSTRACT

A healthcare communication system includes a first plurality of computer devices operable as a nurse call system. The first plurality of computer devices has core nurse call functionality. The system also includes a second plurality of computer devices communicatively coupled to the first plurality of computer devices. The first plurality of computer devices are interconnected logically and/or physically in a tiered architecture arrangement to provide fault isolation among the tiers so that faults occurring in computer devices of one tier don't affect the operability of computer devices in other tiers and so that faults occurring in any of the second plurality of computer devices don't affect the core nurse call functionality of the first plurality of computer devices.

20 Claims, 4 Drawing Sheets

(56) References Cited

U.S. PATENT DOCUMENTS

| | | |
|---|---|---|
| 2,736,888 A | 2/1956 | McLain |
| 2,896,021 A | 7/1959 | Philipps |
| 3,098,220 A | 7/1963 | De Graaf |
| 3,439,320 A | 4/1969 | Ward |
| 3,478,344 A | 11/1969 | Schwitzgebel et al. |
| 3,553,383 A | 1/1971 | Rochtus |
| 3,599,199 A | 8/1971 | Bunting |
| 3,599,200 A | 8/1971 | Bunting |
| 3,696,384 A | 10/1972 | Lester |
| 3,739,329 A | 6/1973 | Lester |
| 3,767,859 A | 10/1973 | Doering et al. |
| 3,805,265 A | 4/1974 | Lester |
| 3,913,153 A | 10/1975 | Adams et al. |
| 3,973,200 A | 8/1976 | Akerberg |
| 4,067,005 A | 1/1978 | Levy et al. |
| 4,150,284 A | 4/1979 | Trenkler et al. |
| 4,151,407 A | 4/1979 | McBride et al. |
| 4,183,015 A | 1/1980 | Drew et al. |
| 4,216,462 A | 8/1980 | McGrath et al. |
| 4,225,953 A | 9/1980 | Simon et al. |
| 4,228,426 A | 10/1980 | Roberts |
| 4,237,344 A | 12/1980 | Moore |
| 4,264,982 A | 4/1981 | Sakarya |
| 4,275,385 A | 6/1981 | White |
| 4,279,433 A | 7/1981 | Petaja |
| 4,298,863 A | 11/1981 | Natitus et al. |
| 4,331,953 A | 5/1982 | Blevins et al. |
| 4,356,475 A | 10/1982 | Neumann et al. |
| 4,418,334 A | 11/1983 | Burnett |
| 4,455,548 A | 6/1984 | Burnett |
| 4,489,387 A | 12/1984 | Lamb et al. |
| 4,495,495 A | 1/1985 | Ormanns et al. |
| 4,495,496 A | 1/1985 | Miller, III |
| 4,539,560 A | 9/1985 | Fleck et al. |
| 4,577,185 A | 3/1986 | Andersen |
| 4,578,671 A | 3/1986 | Flowers |
| 4,593,273 A | 6/1986 | Narcisse |
| 4,598,275 A | 7/1986 | Ross et al. |
| 4,601,064 A | 7/1986 | Shipley |
| 4,649,385 A | 3/1987 | Aires et al. |
| 4,680,790 A | 7/1987 | Packard et al. |
| 4,709,330 A | 11/1987 | Yokoi et al. |
| 4,740,788 A | 4/1988 | Konneker |
| 4,752,951 A | 6/1988 | Konneker |
| 4,792,798 A | 12/1988 | Wilowski |
| 4,795,905 A | 1/1989 | Zierhut |
| 4,814,751 A | 3/1989 | Hawkins et al. |
| 4,833,452 A | 5/1989 | Currier |
| 4,833,467 A | 5/1989 | Kobayashi et al. |
| 4,837,568 A | 6/1989 | Snaper |
| 4,853,692 A | 8/1989 | Wolk et al. |
| 4,899,135 A | 2/1990 | Chahariiran |
| 4,907,845 A | 3/1990 | Wood |
| 4,947,152 A | 8/1990 | Hodges |
| 4,955,000 A | 9/1990 | Nastrom |
| 4,967,195 A | 10/1990 | Shipley |
| 4,990,892 A | 2/1991 | Guest et al. |
| 4,998,095 A | 3/1991 | Shields |
| 4,998,939 A | 3/1991 | Potthast et al. |
| 5,006,830 A | 4/1991 | Merritt |
| 5,027,314 A | 6/1991 | Linwood et al. |
| 5,041,086 A | 8/1991 | Koenig et al. |
| 5,062,151 A | 10/1991 | Shipley |
| 5,065,154 A | 11/1991 | Kaiser |
| 5,075,523 A | 12/1991 | Ford |
| 5,086,290 A | 2/1992 | Murray et al. |
| 5,103,108 A | 4/1992 | Crimmins |
| 5,124,991 A | 6/1992 | Allen |
| 5,137,033 A | 8/1992 | Norton |
| 5,140,309 A | 8/1992 | Gusakov |
| 5,153,584 A | 10/1992 | Engira |
| 5,235,258 A | 8/1993 | Schuerch |
| 5,266,944 A | 11/1993 | Carroll et al. |
| 5,276,680 A | 1/1994 | Messenger |
| 5,291,399 A | 3/1994 | Chaco |
| 5,319,355 A | 6/1994 | Russek |
| 5,319,363 A | 6/1994 | Welch et al. |
| 5,327,592 A | 7/1994 | Stump |
| 5,351,439 A | 10/1994 | Takeda et al. |
| 5,357,254 A | 10/1994 | Kah, Jr. |
| 5,375,604 A | 12/1994 | Kelly et al. |
| 5,396,224 A | 3/1995 | Dukes et al. |
| 5,396,227 A | 3/1995 | Carroll et al. |
| 5,416,695 A | 5/1995 | Stutman et al. |
| 5,430,900 A | 7/1995 | Kim |
| 5,434,775 A | 7/1995 | Sims et al. |
| 5,446,678 A | 8/1995 | Saltzstein et al. |
| 5,455,560 A | 10/1995 | Owen |
| 5,458,123 A | 10/1995 | Unger |
| 5,461,390 A | 10/1995 | Hoshen |
| 5,475,367 A | 12/1995 | Prevost |
| 5,511,256 A | 4/1996 | Capaldi |
| 5,534,851 A | 7/1996 | Russek |
| 5,537,459 A | 7/1996 | Price et al. |
| 5,548,637 A | 8/1996 | Heller et al. |
| 5,549,113 A | 8/1996 | Halleck et al. |
| 5,561,412 A | 10/1996 | Novak et al. |
| 5,564,108 A | 10/1996 | Hunsaker et al. |
| 5,568,119 A | 10/1996 | Schipper et al. |
| 5,576,452 A | 11/1996 | Dever et al. |
| 5,576,952 A | 11/1996 | Stutman et al. |
| 5,579,001 A | 11/1996 | Dempsey et al. |
| 5,588,005 A | 12/1996 | Ali et al. |
| 5,594,786 A | 1/1997 | Chaco et al. |
| 5,600,214 A | 2/1997 | Fromson |
| 5,621,388 A | 4/1997 | Sherburne et al. |
| 5,635,907 A | 6/1997 | Bernard et al. |
| 5,636,245 A | 6/1997 | Ernst et al. |
| 5,640,953 A | 6/1997 | Bishop et al. |
| 5,649,833 A | 7/1997 | Pfeuffer et al. |
| 5,650,769 A | 7/1997 | Campana, Jr. |
| 5,650,770 A | 7/1997 | Schlager et al. |
| 5,664,270 A | 9/1997 | Bell et al. |
| 5,682,139 A | 10/1997 | Pradeep et al. |
| 5,686,888 A | 11/1997 | Welles, II |
| 5,686,902 A | 11/1997 | Reis et al. |
| 5,687,734 A | 11/1997 | Dempsey et al. |
| 5,689,229 A | 11/1997 | Chaco et al. |
| 5,691,980 A | 11/1997 | Welles, II et al. |
| 5,699,038 A | 12/1997 | Ulrich et al. |
| 5,705,980 A | 1/1998 | Shapiro |
| 5,708,421 A | 1/1998 | Boyd |
| 5,713,856 A | 2/1998 | Eggers et al. |
| 5,714,548 A | 2/1998 | Ma et al. |
| 5,719,761 A | 2/1998 | Gatti et al. |
| 5,731,757 A | 3/1998 | Layson, Jr. |
| 5,742,237 A | 4/1998 | Bledsoe |
| 5,751,246 A | 5/1998 | Hertel |
| 5,752,917 A | 5/1998 | Fuchs |
| 5,760,704 A | 6/1998 | Barton et al. |
| 5,767,791 A | 6/1998 | Stoop et al. |
| 5,781,442 A | 7/1998 | Engleson et al. |
| 5,781,921 A | 7/1998 | Nichols |
| 5,787,528 A | 8/1998 | Antinori |
| 5,793,290 A | 8/1998 | Eagleson et al. |
| 5,808,564 A | 9/1998 | Simms et al. |
| 5,812,056 A | 9/1998 | Law |
| 5,822,418 A | 10/1998 | Yacenda et al. |
| 5,822,544 A | 10/1998 | Chaco et al. |
| 5,838,223 A | 11/1998 | Gallant et al. |
| 5,844,488 A | 12/1998 | Musick |
| 5,867,821 A | 2/1999 | Ballantyne et al. |
| 5,877,675 A | 3/1999 | Rebstock et al. |
| 5,901,391 A | 5/1999 | Kato |
| 5,933,488 A | 8/1999 | Marcus et al. |
| 5,936,539 A | 8/1999 | Fuchs |
| 5,942,986 A | 8/1999 | Shabot et al. |
| 5,944,659 A | 8/1999 | Flach et al. |
| 5,956,539 A | 9/1999 | Fitterman et al. |
| 5,963,137 A | 10/1999 | Waters, Sr. |
| 5,974,389 A | 10/1999 | Clark et al. |
| 5,991,728 A | 11/1999 | DeBusk et al. |
| 5,995,937 A | 11/1999 | DeBusk et al. |
| 6,014,633 A | 1/2000 | DeBusk et al. |

(56) References Cited

U.S. PATENT DOCUMENTS

| | | |
|---|---|---|
| 6,037,723 A | 3/2000 | Shafer et al. |
| 6,057,758 A | 5/2000 | Dempsey et al. |
| 6,057,782 A | 5/2000 | Koenig |
| 6,067,019 A | 5/2000 | Scott |
| 6,076,166 A | 6/2000 | Moshfeghi et al. |
| 6,078,261 A | 6/2000 | Davsko |
| 6,085,493 A | 7/2000 | DeBusk et al. |
| 6,088,362 A | 7/2000 | Turnbull et al. |
| 6,093,146 A | 7/2000 | Filangeri |
| 6,097,308 A | 8/2000 | Albert et al. |
| 6,101,644 A | 8/2000 | Gagneur et al. |
| 6,111,509 A | 8/2000 | Holmes |
| 6,125,350 A | 9/2000 | Dirbas |
| 6,133,837 A | 10/2000 | Riley |
| 6,147,592 A | 11/2000 | Ulrich et al. |
| 6,183,417 B1 | 2/2001 | Geheb et al. |
| 6,208,250 B1 | 3/2001 | Dixon et al. |
| 6,241,668 B1 | 6/2001 | Herzog |
| 6,259,355 B1 | 7/2001 | Chaco et al. |
| 6,264,614 B1 | 7/2001 | Albert et al. |
| 6,272,347 B1 | 8/2001 | Griffith et al. |
| 6,279,183 B1 | 8/2001 | Kummer et al. |
| 6,287,253 B1 | 9/2001 | Ortega et al. |
| 6,302,844 B1 | 10/2001 | Walker et al. |
| 6,314,556 B1 | 11/2001 | DeBusk et al. |
| 6,320,510 B2 | 11/2001 | Menkedick et al. |
| 6,344,794 B1 | 2/2002 | Ulrich et al. |
| 6,348,777 B1 | 2/2002 | Brown et al. |
| 6,362,725 B1 | 3/2002 | Ulrich et al. |
| 6,364,834 B1 | 4/2002 | Reuss et al. |
| 6,398,727 B1 | 6/2002 | Bui et al. |
| 6,406,426 B1 | 6/2002 | Reuss et al. |
| 6,407,335 B1 | 6/2002 | Franklin-Lees et al. |
| 6,412,980 B1 | 7/2002 | Lounsberry et al. |
| 6,416,471 B1 | 7/2002 | Kumar et al. |
| 6,421,649 B1 | 7/2002 | Rattner |
| 6,439,769 B1 | 8/2002 | Polkus et al. |
| 6,441,742 B1 | 8/2002 | Lovely et al. |
| 6,442,290 B1 | 8/2002 | Ellis et al. |
| 6,445,299 B1 | 9/2002 | Rojas, Jr. |
| 6,450,956 B1 | 9/2002 | Rappaport et al. |
| 6,462,656 B2 | 10/2002 | Ulrich et al. |
| 6,483,264 B1 | 11/2002 | Shafer et al. |
| 6,486,792 B1 | 11/2002 | Moster et al. |
| 6,493,568 B1 | 12/2002 | Bell et al. |
| 6,494,831 B1 | 12/2002 | Koritzinsky |
| 6,510,344 B1 | 1/2003 | Halpern |
| 6,516,324 B1 | 2/2003 | Jones et al. |
| 6,526,310 B1 | 2/2003 | Carter et al. |
| 6,529,164 B1 | 3/2003 | Carter |
| 6,533,453 B1 | 3/2003 | Heidsieck et al. |
| 6,535,576 B2 | 3/2003 | Vafi et al. |
| 6,539,393 B1 | 3/2003 | Kabala |
| 6,544,173 B2 | 4/2003 | West et al. |
| 6,544,174 B2 | 4/2003 | West et al. |
| 6,551,243 B2 | 4/2003 | Bocionek et al. |
| 6,553,105 B2 | 4/2003 | Chea, Jr. et al. |
| 6,553,106 B1 | 4/2003 | Gould et al. |
| 6,554,174 B2 | 4/2003 | Aceves |
| 6,556,630 B1 | 4/2003 | Brinsfield et al. |
| 6,560,224 B1 | 5/2003 | Kung et al. |
| 6,560,274 B1 | 5/2003 | Leitgeb et al. |
| 6,572,556 B2 | 6/2003 | Stoycos et al. |
| 6,575,901 B2 | 6/2003 | Stoycos et al. |
| 6,581,204 B2 | 6/2003 | DeBusk et al. |
| 6,584,182 B2 | 6/2003 | Brodnick |
| 6,584,454 B1 | 6/2003 | Hummel, Jr. et al. |
| 6,585,645 B2 | 7/2003 | Hutchinson |
| 6,589,170 B1 | 7/2003 | Flach et al. |
| 6,593,528 B2 | 7/2003 | Franklin-Lees et al. |
| 6,594,146 B2 | 7/2003 | Frangesch et al. |
| 6,594,519 B2 | 7/2003 | Stoycos et al. |
| 6,600,421 B2 | 7/2003 | Freeman |
| 6,603,494 B1 | 8/2003 | Banks et al. |
| 6,609,115 B1 | 8/2003 | Mehring et al. |
| 6,616,606 B1 | 9/2003 | Petersen et al. |
| 6,622,088 B2 | 9/2003 | Hood |
| 6,640,246 B1 | 10/2003 | Gary, Jr. et al. |
| 6,643,238 B2 | 11/2003 | Nakajima |
| 6,650,346 B1 | 11/2003 | Jaeger et al. |
| 6,659,947 B1 | 12/2003 | Carter et al. |
| 6,665,358 B1 | 12/2003 | Oldagiri |
| 6,665,385 B2 | 12/2003 | Rogers et al. |
| 6,665,820 B1 | 12/2003 | Frowein et al. |
| 6,669,630 B1 | 12/2003 | Joliat et al. |
| 6,671,547 B2 | 12/2003 | Lyster et al. |
| 6,671,563 B1 | 12/2003 | Engelson et al. |
| 6,685,633 B2 | 2/2004 | Albert et al. |
| 6,689,091 B2 | 2/2004 | Bui et al. |
| 6,693,514 B2 | 2/2004 | Perea, Jr. et al. |
| 6,694,367 B1 | 2/2004 | Miesbauer et al. |
| 6,694,509 B1 | 2/2004 | Stoval et al. |
| 6,697,765 B2 | 2/2004 | Kuth |
| 6,707,476 B1 | 3/2004 | Hochstedler |
| 6,714,913 B2 | 3/2004 | Brandt et al. |
| 6,721,818 B1 | 4/2004 | Nakamura |
| 6,726,634 B2 | 4/2004 | Freeman |
| 6,727,818 B1 | 4/2004 | Wildman et al. |
| 6,731,311 B2 | 5/2004 | Bufe et al. |
| 6,731,989 B2 | 5/2004 | Engleson et al. |
| 6,740,033 B1 | 5/2004 | Olejniczak et al. |
| 6,749,566 B2 | 6/2004 | Russ |
| 6,751,630 B1 | 6/2004 | Franks et al. |
| 6,754,545 B2 | 6/2004 | Haeuser et al. |
| 6,754,883 B2 | 6/2004 | DeBusk et al. |
| 6,759,607 B2 | 7/2004 | Engler |
| 6,759,959 B2 | 7/2004 | Wildman |
| 6,763,541 B2 | 7/2004 | Mahoney et al. |
| 6,771,172 B1 | 8/2004 | Robinson et al. |
| 6,773,396 B2 | 8/2004 | Flach et al. |
| 6,778,225 B2 | 8/2004 | David |
| 6,781,517 B2 | 8/2004 | Moster et al. |
| 6,784,797 B2 | 8/2004 | Smith et al. |
| 6,788,206 B1 | 9/2004 | Edwards |
| 6,791,460 B2 | 9/2004 | Dixon et al. |
| 6,792,396 B2 | 9/2004 | Inda et al. |
| 6,801,227 B2 | 10/2004 | Bocionek et al. |
| 6,807,543 B2 | 10/2004 | Muthya |
| 6,825,763 B2 | 11/2004 | Ulrich et al. |
| 6,826,578 B2 | 11/2004 | Brackett et al. |
| 6,828,992 B1 | 12/2004 | Freeman et al. |
| 6,829,796 B2 | 12/2004 | Salvatini et al. |
| 6,830,549 B2 | 12/2004 | Bui et al. |
| 6,832,199 B1 | 12/2004 | Kucek et al. |
| 6,840,117 B2 | 1/2005 | Hubbard, Jr. |
| 6,847,814 B1 | 1/2005 | Vogeleisen |
| 6,864,795 B2 | 3/2005 | Smith et al. |
| 6,868,256 B2 | 3/2005 | Dooley et al. |
| 6,870,484 B1 | 3/2005 | Brinsfield et al. |
| 6,871,211 B2 | 3/2005 | Labounty et al. |
| 6,873,884 B2 | 3/2005 | Brackett et al. |
| 6,876,303 B2 | 4/2005 | Reeder et al. |
| 6,876,985 B2 | 4/2005 | Kawanaka |
| 6,885,288 B2 | 4/2005 | Pincus |
| 6,891,909 B2 | 5/2005 | Hurley et al. |
| 6,892,083 B2 | 5/2005 | Shostak |
| 6,897,780 B2 | 5/2005 | Ulrich et al. |
| 6,904,161 B1 | 6/2005 | Becker et al. |
| 6,909,995 B2 | 6/2005 | Shiraishi |
| 6,912,549 B2 | 6/2005 | Rotter et al. |
| 6,915,170 B2 | 7/2005 | Engleson et al. |
| 6,925,367 B2 | 8/2005 | Fontius |
| 6,930,878 B2 | 8/2005 | Brackett et al. |
| 6,958,706 B2 | 10/2005 | Chaco et al. |
| 6,968,375 B1 | 11/2005 | Brown |
| 6,982,639 B2 | 1/2006 | Brackett et al. |
| 6,988,989 B2 | 1/2006 | Weiner et al. |
| 6,998,986 B2 | 2/2006 | Smith |
| 7,020,921 B2 | 4/2006 | Wang |
| 7,023,821 B2 | 4/2006 | Wotherspoon et al. |
| 7,038,584 B2 | 5/2006 | Carter |
| 7,053,767 B2 | 5/2006 | Petite et al. |
| 7,061,396 B1 | 6/2006 | Conrad et al. |
| 7,068,143 B2 | 6/2006 | Doering et al. |

(56) References Cited

U.S. PATENT DOCUMENTS

| | | |
|---|---|---|
| 7,071,820 B2 | 7/2006 | Callaway |
| 7,079,036 B2 | 7/2006 | Cooper et al. |
| 7,088,235 B1 | 8/2006 | Carricut |
| 7,092,376 B2 | 8/2006 | Schuman |
| 7,107,642 B2 | 9/2006 | Wong et al. |
| 7,138,902 B2 | 11/2006 | Menard |
| 7,151,457 B2 | 12/2006 | Riley et al. |
| 7,160,133 B2 | 1/2007 | Karadimas et al. |
| 7,242,308 B2 | 7/2007 | Ulrich et al. |
| 7,248,881 B2 | 7/2007 | Shostak |
| 7,263,669 B2 | 8/2007 | Denholm |
| 7,275,220 B2 | 9/2007 | Brummel et al. |
| 7,290,299 B2 | 11/2007 | Votel |
| 7,292,135 B2 | 11/2007 | Bixler et al. |
| 7,299,512 B2 | 11/2007 | Cavalier et al. |
| 7,301,451 B2 | 11/2007 | Hastings |
| 7,307,522 B2 | 12/2007 | Dawson |
| 7,310,541 B2 | 12/2007 | Shostak |
| 7,319,386 B2 | 1/2008 | Collins, Jr. et al. |
| 7,333,002 B2 | 2/2008 | Bixler et al. |
| 7,336,187 B2 | 2/2008 | Hubbard, Jr. et al. |
| 8,046,625 B2 | 10/2011 | Ferguson et al. |
| 8,392,747 B2 | 3/2013 | Ferguson et al. |
| 2001/0050610 A1 | 12/2001 | Gelston |
| 2001/0051765 A1 | 12/2001 | Walker et al. |
| 2002/0014951 A1 | 2/2002 | Kramer et al. |
| 2002/0032583 A1 | 3/2002 | Joao |
| 2002/0044043 A1 | 4/2002 | Chaco et al. |
| 2002/0044059 A1 | 4/2002 | Reeder et al. |
| 2002/0067273 A1 | 6/2002 | Jaques et al. |
| 2002/0070867 A1 | 6/2002 | Conway et al. |
| 2002/0080037 A1 | 6/2002 | Dixon et al. |
| 2002/0101349 A1 | 8/2002 | Rojas, Jr. |
| 2002/0103674 A1 | 8/2002 | Reeder et al. |
| 2002/0151990 A1 | 10/2002 | Ulrich et al. |
| 2002/0173991 A1 | 11/2002 | Avitall |
| 2002/0186136 A1 | 12/2002 | Schuman |
| 2002/0196141 A1 | 12/2002 | Boone et al. |
| 2003/0010345 A1 | 1/2003 | Koblasz et al. |
| 2003/0028449 A1 | 2/2003 | Heinen et al. |
| 2003/0030569 A1 | 2/2003 | Ulrich et al. |
| 2003/0052787 A1 | 3/2003 | Zerhusen et al. |
| 2003/0074222 A1 | 4/2003 | Rosow et al. |
| 2003/0146835 A1 | 8/2003 | Carter |
| 2003/0149598 A1 | 8/2003 | Santoso et al. |
| 2003/0176798 A1 | 9/2003 | Simon |
| 2003/0179099 A1 | 9/2003 | Perea, Jr. et al. |
| 2003/0197614 A1 | 10/2003 | Smith et al. |
| 2003/0206116 A1 | 11/2003 | Weiner et al. |
| 2003/0212575 A1 | 11/2003 | Saalsaa et al. |
| 2003/0230469 A1 | 12/2003 | Engler |
| 2004/0064890 A1 | 4/2004 | Kim et al. |
| 2004/0158922 A1 | 8/2004 | Eberler et al. |
| 2004/0183681 A1 | 9/2004 | Smith |
| 2004/0183684 A1 | 9/2004 | Callaway |
| 2004/0186358 A1 | 9/2004 | Chernow et al. |
| 2004/0193449 A1 | 9/2004 | Wildman et al. |
| 2004/0222897 A1 | 11/2004 | Schuhmann et al. |
| 2004/0243446 A1 | 12/2004 | Wyatt |
| 2004/0249670 A1 | 12/2004 | Noguchi et al. |
| 2004/0261184 A1 | 12/2004 | Flick |
| 2005/0035862 A1 | 2/2005 | Wildman et al. |
| 2005/0055779 A1 | 3/2005 | Damewood |
| 2005/0076441 A1 | 4/2005 | Dominati et al. |
| 2005/0110617 A1 | 5/2005 | Kile et al. |
| 2005/0155149 A1 | 7/2005 | Pedersen |
| 2005/0170863 A1 | 8/2005 | Shostak |
| 2005/0206505 A1 | 9/2005 | Arcaria |
| 2005/0242946 A1 | 11/2005 | Hubbard, Jr. et al. |
| 2006/0046579 A1 | 3/2006 | Karadimas et al. |
| 2006/0049936 A1 | 3/2006 | Collins, Jr. et al. |
| 2006/0114854 A1 | 6/2006 | Wotherspoon et al. |
| 2006/0126560 A1 | 6/2006 | Wotherspoon et al. |
| 2006/0136265 A1 | 6/2006 | Summers et al. |
| 2006/0214786 A1 | 9/2006 | Bixler et al. |
| 2006/0220798 A1 | 10/2006 | Willis |
| 2006/0239195 A1 | 10/2006 | Camins et al. |
| 2006/0248221 A1 | 11/2006 | Hottel et al. |
| 2006/0267740 A1 | 11/2006 | Bixler et al. |
| 2007/0071114 A1 | 3/2007 | Sanderford, Jr. et al. |
| 2007/0135688 A1 | 6/2007 | Brown |
| 2007/0156456 A1 | 7/2007 | McGillin et al. |
| 2007/0210917 A1 | 9/2007 | Collins, Jr. et al. |
| 2007/0229249 A1 | 10/2007 | McNeal et al. |
| 2007/0237487 A1 | 10/2007 | Lin |
| 2007/0239484 A1 | 10/2007 | Around et al. |
| 2007/0257788 A1 | 11/2007 | Carlson et al. |
| 2008/0004904 A1 | 1/2008 | Tran |
| 2008/0015900 A1 | 1/2008 | Denholm |
| 2008/0018436 A1 | 1/2008 | Traughber et al. |
| 2008/0027754 A1 | 1/2008 | Auker et al. |
| 2009/0217080 A1 | 8/2009 | Ferguson et al. |

FOREIGN PATENT DOCUMENTS

| | | |
|---|---|---|
| JP | 1-76197 | 3/1989 |
| WO | WO 95/23378 | 8/1995 |
| WO | WO 98/08203 | 2/1998 |
| WO | WO 02/091297 | 11/2002 |
| WO | WO 2004/036390 | 4/2004 |

OTHER PUBLICATIONS

Hill-Rom A Hillenbrand Industry, The COMposer Communication System Service Manual, 1995.

Hill-Rom A Hillenbrand Industry, COMLinx™ Enterprise Solutions Nurse Communication Module, User's Guide, 2000.

European Search Report for EP 09 25 0419, dated Aug. 13, 2010, (7 pages).

Partial European Search report from EP 09 25 0420 date Jun. 16, 2009.

(Online) XP002530934 Hill-Rom Technical Brief, www.hill-rom/canada/PDF/144097.pdf, :CONLinx Nurse Communication Module Technological Advances, Jul. 13, 2006, 4 pages.

European Search Report for European Patent Application No. 12164812.5, dated Mar. 9, 2012, 8 pages.

European Search Report for European Patent Application No. 12164815.8, dated Mar. 9, 2012, 8 pages.

European Search Report for European Patent Application No. 12164817.4, dated Mar. 9, 2012, 9 pages.

DISTRIBUTED FAULT TOLERANT ARCHITECTURE FOR A HEALTHCARE COMMUNICATION SYSTEM

This application is a continuation of U.S. application Ser. No. 13/241,461, filed Sep. 23, 2011, now U.S. Pat. No. 8,392,747, which is a continuation of U.S. application Ser. No. 12/369,818, filed Feb. 12, 2009, now U.S. Pat. No. 8,046,625, which claims the benefit, under 35 U.S.C. §119(e), of U.S. Provisional Patent Application Nos. 61/066,877, 61/066,882, 61/066,883, and 61/066,918, each of which was filed Feb. 22, 2008, and U.S. Provisional Patent Application No. 61/145,306, which was filed Jan. 16, 2009, the disclosures of all of which are hereby expressly incorporated by reference herein.

BACKGROUND

The present disclosure relates to healthcare communication systems, such as nurse call systems. In particular the present disclosure relates to healthcare communication systems having a master station and devices in patient rooms that communicate with the master station.

Most hospitals and other types of in-patient healthcare facilities have some sort of a nurse call system. Patients place nurse calls by pressing a nurse call button located on a hospital bed or on a hand-held unit, known in the art as a pillow speaker or pillow speaker unit, or by actuating a wall mounted switch. After a patient places a nurse call, a caregiver at a master station may answer the nurse call which enables voice communications between the caregiver at the master station and the patient. To facilitate such voice communications a microphone and speaker is located somewhere in the patient room. Oftentimes the microphone and speaker are included in the pillow speaker unit or in an audio station mounted to a wall of the patient or to headwall unit which is, in turn, mounted to a wall of the patient room.

One example of a known nurse call system is Hill-Rom's COMLINX® system. In addition to the voice communication function, the COMLINX system is connected to the patient's hospital bed to receive bed status information regarding various aspects of the hospital bed such as the position of the siderails of the bed (e.g., up or down), whether the bed's casters are braked or released, whether or not an upper frame of the bed is in its lowest position, and so forth. See, for example, U.S. Pat. Nos. 7,242,308; 6,897,780; 6,362,725; 6,147,592; 5,838,223; 5,699,038; and 5,561,412, which relate to the COMLINX system. Another example of a known nurse call system is G.E. Healthcare's TELLIGENCE™ system.

SUMMARY

The present invention comprises a healthcare communication system and/or method, or a component thereof, that has any one or more of the features listed in the appended claims and/or any one or more of the following features, which alone or in any combination may comprise patentable subject matter:

A healthcare communication system may comprise a first plurality of computer devices that are operable as a nurse call system. The first plurality of computer devices may have core nurse call functionality residing on an embedded computing platform. The first plurality of computer devices may include patient stations, staff stations, or master stations of the nurse call system and any of these stations may have a graphical display screen. The healthcare communication system may have a second plurality of computer devices that are operable to provide the first plurality of computer devices with additional functionality via software plug-ins that are transmitted to one or more of the first plurality of computer devices. Some or all of the second plurality of computer devices may be part of an Ethernet of the healthcare facility.

Use of a user interface displayed on the graphical display screen may result in at least one of the software plug-ins being transmitted to at least one of the first plurality of computer devices. The first plurality of computer devices may include an input/output (I/O) circuit that is coupled to an associated patient station. Some of the software plug-ins may be operable to change the user interface of the graphical display screen to a different user interface. In response to a new computer device being added to the first plurality of computer devices, such as connecting a new patient station or staff station to the nurse call system, at least one of the second plurality of computer devices automatically transmits at least one software plug-in to the new computer device.

The additional functionality of the second plurality of computer devices may reside on a server computing platform. The second plurality of software devices may be configured such that at least one of the software plug-ins is transmitted to the first plurality of computer devices on an as needed basis as dictated by use of at least one of the first plurality of computer devices. Additionally or alternatively, the second plurality of software devices may be configured such that at least one of the software plug-ins is transmitted to some or all of the first plurality of computer devices in response to use of at least one of the second plurality of computer devices. Software upgrades or updates installed on at least one of the second plurality of computer devices may be distributed automatically to at least some of the first plurality of computer devices. The software upgrades or updates may also be distributed automatically to at least one other computer device of the second plurality of computer devices.

The core nurse call functionality may comprise functionality regulated by a regulations entity, such as a governmental body or standards setting organization such as Underwriter's Laboratories, and the additional functionality may comprise non-regulated functionality. For example, in some embodiments, the first plurality of computer devices may be compliant with the Underwriter's Laboratories UL-1069 standard.

The first plurality of computer devices and/or the second plurality of computer devices may incorporate Publish and Subscribe (PubSub) data communication technology. The PubSub data communication technology permits at least one computer device of the first plurality of computer devices to publish data to, and/or to subscribe to data from, at least one computer device of the second plurality of computer devices, and vice versa. At least one of the first plurality of computer devices may be communicatively coupled to a hospital bed and may receive bed status data from the hospital bed.

At least one computer device of the first plurality of computer devices may have auto-discovery software that is operable, in response to installation of the at least on computer in the nurse call system, to detect network connectivity and to initiate communications with a device manager. The device manager may be operable to provide software modules and/or network settings to the at least one computer device of the first plurality of computer devices The healthcare communication system may have at least one additional computer device that may be coupled to at least one of the computer devices of the first plurality or second plurality of computer devices and that may incorporate a software-based or hard-ware based Session Initiation Protocol (SIP) voice over Internet protocol (VoIP) to separate the setting up and tearing down of voice calls between SIP enabled voice endpoint devices. The at least one additional computer device may comprise, for example, a VoIP private branch exchange (PBX). At least one of the first computer devices may comprise a VoIP room gateway that is operable to distribute communication data to multiple voice terminals or VoIP voice endpoints installed in patient rooms and hallways.

The first plurality of computer devices may be interconnected logically and/or physically in a tiered architecture arrangement to provide fault isolation among the tiers so that faults occurring in computer devices of one tier don't affect the operability of computer devices in other tiers and/or so that faults occurring in any of the second plurality of computer devices don't affect the core nurse call functionality of the first plurality of computer devices.

At least one of the tiers in such an arrangement may comprise a subset of the first plurality of computer devices that are associated with a patient room. Another of the tiers in such an arrangement may comprise a subset of the first plurality of computer devices that are associated with a nursing unit having a plurality of patient rooms.

At least one computer device of the first plurality of second plurality of computer devices may comprise a server that is equipped with Redundant Arrays of Independent Disks or Drives (RAID), redundant power supplies, and/or clustering failover capability. At least one computer device of the first plurality of second plurality of computer devices may comprise broker service software that may be operable to monitor other services on the first plurality and/or second plurality of computer devices and that may repair or restart faulty services.

Additional features, which alone or in combination with any other feature(s), such as those listed above, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures, in which.

DETAILED DESCRIPTION

Figure 1:
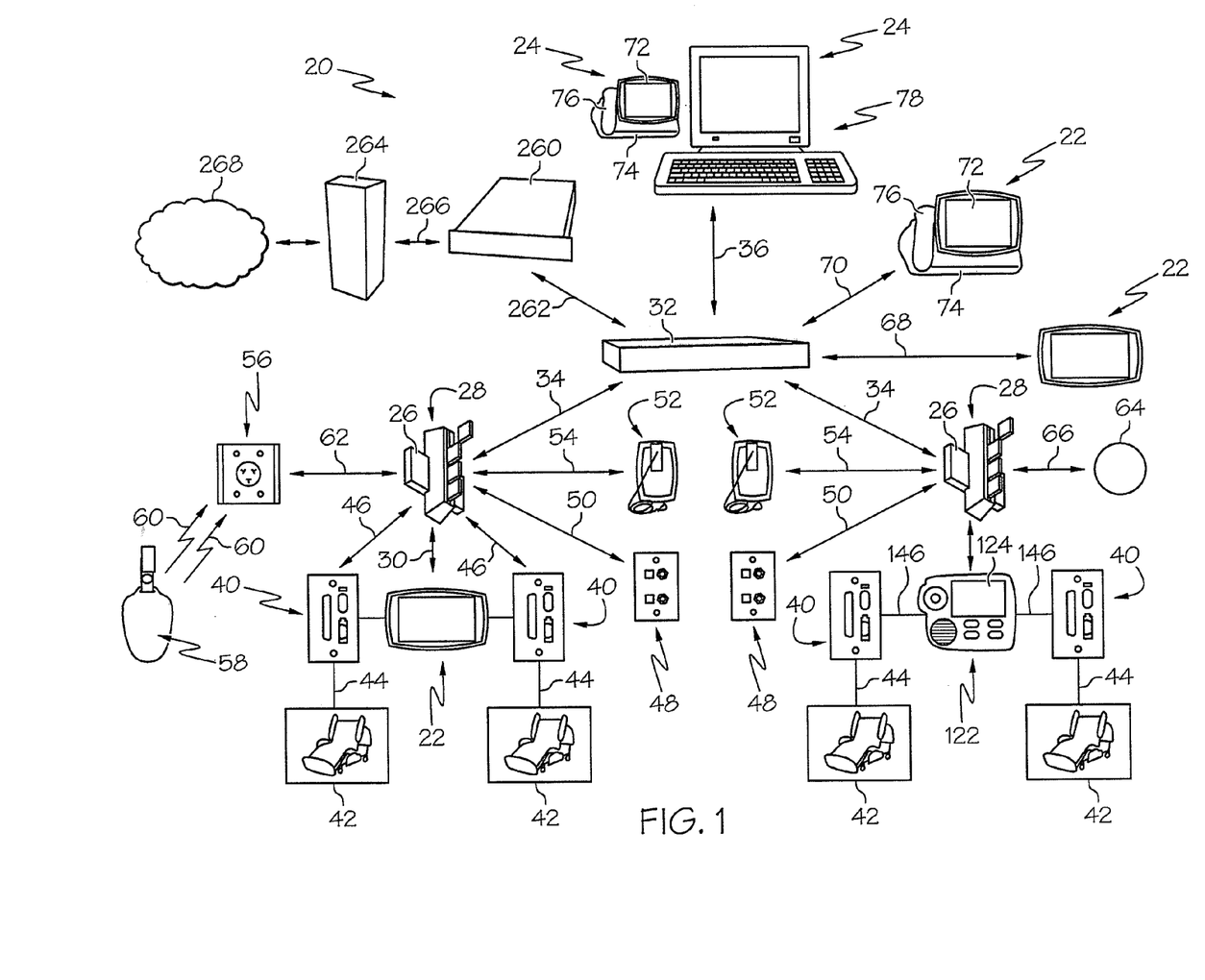
FIG. 1 is a block diagram showing various components of a nurse call system, some of which are included as a part of a healthcare communication system according to this disclosure.

A healthcare communication system 20 includes a plurality of graphical audio stations 22 and a master station or console 24 which are communicatively coupled as shown diagrammatically in FIG. 1. Many of the stations 22 are located in patient rooms and are mounted, for example, to a wall of the respective room or to a headwall unit that, in turn, is mounted to a wall of the respective room. Stations 22 may be mounted to other architectural support structures, such as service chases or columns just to name a couple. Stations 22 may be located in other areas of the healthcare facility as well, such as in staff work areas including, for example, hallways and staff lounges. The stations 22 located in patient rooms may sometimes be referred to herein as patient stations 22, whereas the stations 22 located in staff work areas may be sometimes be referred to herein as staff stations 22. The functionality of stations 22 described herein is applicable to all stations 22 regardless of whether the station 22 is a patient station 22 or a staff station 22, unless specifically noted otherwise.

Patient stations 22 communicate bidirectionally (e.g., two-way communication) with an input/output (I/O) circuit 27 which is located within a housing 26 mounted near a dome light assembly 28. The bidirectional communication is indicated diagrammatically in FIG. 1 by double headed arrow 30. I/O circuit 27 is also shown diagrammatically in FIG. 2. Dome light assemblies 28 are typically mounted outside respective patient rooms near the doorways of the rooms and are readily visible to caregivers in the hallway to determine whether any calls or other events indicated on the dome light are occurring within the associated room. Thus, housings 26 with I/O circuit 27 therein are mounted generally at these same locations outside patient rooms. Additional details of the dome light assemblies 28, housing 26, and circuit board 27 are provided in U.S. Provisional Patent Application No. 61/066,883 which was filed Feb. 22, 2008, which was titled "Indicator Assembly for Healthcare Communication System," and which is already incorporated by reference herein.

A 9-page electric circuit schematic illustrating one possible electric circuit implementation of one embodiment of the circuitry of dome light assembly 28 is shown in FIG. 12 of U.S. Provisional Patent Application No. 61/066,877, which was filed Feb. 22, 2008, which was titled "Distributed Healthcare Communication System," and which is already incorporated by reference herein. In one embodiment, dome light assembly 28 is, for example, an International Business Machines (IBM) Part No. 43T1899 dome light fixture. A 55-page electric circuit schematic illustrating one possible electric circuit implementation of input/output (I/O) circuit 27 according to this disclosure is shown in FIG. 15 of U.S. Provisional Patent Application No. 61/066,877 which is already incorporated by reference herein. In one embodiment, I/O circuit 27 is, for example, an IBM part no. 43T2063 IO Board. In some Appendices of the written description of U.S. Provisional Patent Application No. 61/066,877, I/O circuit 27 may be referred to as an I/O board or an I/O circuit board. However, this is not to imply that all circuit components of the circuitry of I/O circuit 27 need to be on a single circuit board, but that is certainly one possibility. Thus, in some contemplated embodiments I/O circuitry 27 may be distributed among numerous circuit boards, and in other contemplated embodiments some or all of the components of circuit 27 may not be on any circuit board at all. While illustrative circuit 27 is located in housing 26, it is within the scope of this disclosure for various components of circuit 27 to be located in separate housings.

The I/O circuit 27 of assembly 28 communicates bidirectionally with a Power over Ethernet (PoE) switch 32 as indicated diagrammatically in FIG. 1 by double headed arrow 34. PoE switch 32 communicates bidirectionally with master station 24 as indicated diagrammatically by double headed arrow 36. Suitable PoE switches are available from a variety of suppliers and may include, for example, the PoE switch marketed by Hill-Rom Company, Inc. in connection with its NaviCare® Nurse Call™ system or such as one or more of the various Dell PoE switches marketed under the PowerConnect™ brand name. Optionally, an external power supply is coupled to PoE switch 32 to provide back up power to PoE switch 32 in the event that an internal power supply of PoE switch 32 fails. One example of a suitable external power supply is Optimal Power part number OPN300-48SN which is coupled to the PoE switch 32 using an Optimal Power part number OPNC30148 cable. While only one patient station 22 is shown in FIG. 1 as being communicatively coupled to master station 24, via the I/O circuit board 27 of assembly 28 and via PoE switch 32, it will be appreciated that system 20 may have numerous such patient stations 22 that may communicate with master station 24 via respective I/O circuit boards 27 and via PoE switch 32.

Typically, all of the patient stations 22 of a nursing unit communicate with the same master station 24. The master stations 24 and graphical audio stations 22 of different nursing units may be coupled together by interconnecting the respective PoE switches as indicated diagrammatically in FIG. 3 via dotted lines 38. In this way, information can be shared, and communications established, between computers devices, such as stations 22, of different nursing units. This is an improvement over prior art systems having the master stations and audio stations of each nursing unit isolated and unable to communicate with the master stations and audio stations of other nursing units.

Figure 2:
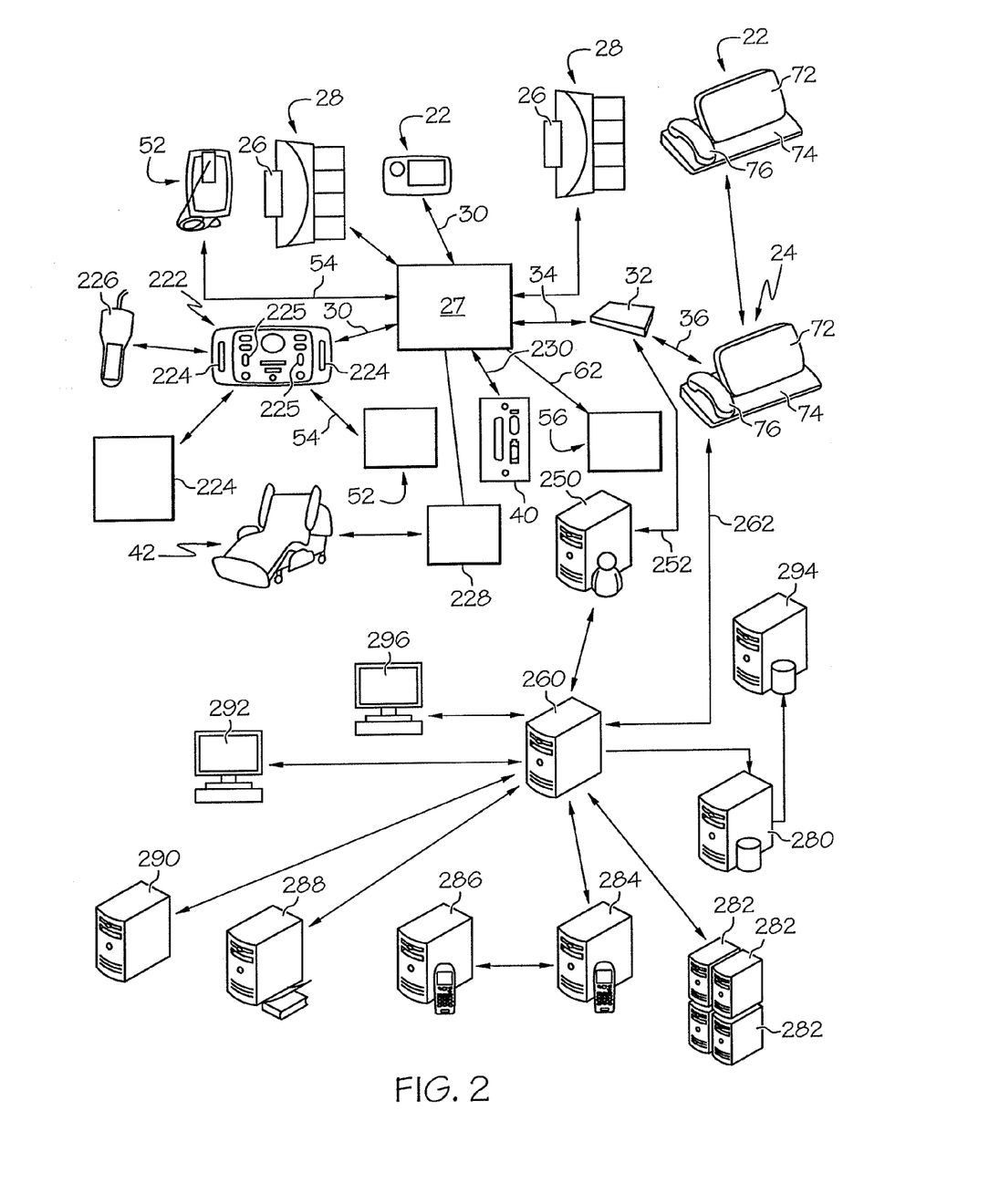
FIG. 2 is a block diagram showing a master console of the nurse call system coupling the nurse call system to other computer devices included in a computer network of the healthcare facility.

In some embodiments, such as the one shown in FIG. 1, system 20 includes bed connector units 40, each of which is communicatively coupled to an associated hospital bed 42 as shown diagrammatically in FIG. 1 via lines 44. Bed connector units 40 are, in turn coupled to a respective circuit board 27 as indicated diagrammatically in FIG. 1 via lines 46. In some other embodiments, bed connector units 22 may be coupled to graphical audio station 22 which communicates with the corresponding circuit board 27 in the way that bed connector units 40 are shown coupling to graphical audio stations 124 (discussed in further detail below) via diagrammatic lines 146 in FIG. 1. In still other embodiments, bed connectors units 40 may be integrated into a common housing of graphical audio stations 22 (and stations 124 as well) in the way that connectors 224, 225 are integrated into standard audio station 222 as shown in FIG. 2. Stations 222 are discussed in further detail below.

One version of bed connector unit 40 is referred to in some of the Appendices of the written description of U.S. Provisional Patent Application No. 61/066,877 as a Bed Interface Unit (BIU) which, in one embodiment, includes a 37-pin connector to attach to a bed cable, includes another connector for attachment of a call pendant or pillow speaker unit, and an includes a button that can be manually pressed to send and/or cancel a nurse call. Another version of a bed connector 228 is referred to as a Silver Plate in some of the Appendices attached in U.S. Provisional Patent Application No. 61/066, 877 and is shown in FIG. 2. Bed connector 228 is a low cost connector which includes only a connector to which bed 42 couples via a suitable connection cord. In some embodiments, beds 42 comprise one or more of the beds marketed by Hill-Rom Company, Inc. under the brand names TOTALCARE®, VERSACARE®, ADVANCED-1000™, CCUII™ and ADVANTA™.

Many other types of devices in a patient room may also couple to a respective I/O circuit 27 mounted near the corresponding dome light assembly 28 to communicate with master station 24 and, if desired, other computer devices of the a computer network of the healthcare facility. For example, in FIG. 1, an equipment connector 48 to which patient care equipment, such as patient monitoring equipment, may be connected is coupled to the I/O circuit 27 as indicated diagrammatically by double-headed arrow 50 and a wall-mounted nurse call switch 52 which may be mounted in a lavatory of the patient room, for example, is coupled to the circuit board 27 of assembly 28 as indicated diagrammatically by double-headed arrow 54. Furthermore, a wireless receiver 56, which illustratively is an infrared receiver that receives wireless signals 60 from locating-and-tracking badges 58 worn or carried by caregivers is coupled to the I/O circuit 27 of assembly 28 as indicated diagrammatically by double-headed arrow 62. It is also contemplated herein that a smoke alarm 64 is coupleable to the I/O circuit 27 of assembly 28 as indicated in FIG. 1 by double headed arrow 66.

As previously mentioned, some graphical audio stations 22 are located in staff work areas and are referred to as staff stations or consoles 22. In FIG. 1, a first staff station 22 communicates bidirectionally with PoE switch 32 via a communications link 68 and a second staff station 22 communicates bidirectionally with PoE switch 32 via a communications link 70. The first staff station 22 is mounted to a wall, for example, whereas the second staff station 22 has a graphical display screen module 72 connected to a base module 74 which includes a telephone hand set 76. The master station 24 shown in the FIG. 1 example also has a graphical display screen module 72 connected to a base module 74 which has a telephone handset 76. The FIG. 1 example also shows a personal computer 78 which cooperates with the associated display screen module 72 to provide the master station functionality. In other embodiments, personal computer 78 is the only computer device included in master station 24 while, in still other embodiments, personal computer 78 is omitted. Thus, depending upon the manner in which a graphical display module 72 is programmed it can serve as a patient station 22, a staff station 22 or as a master station 24. When serving as a staff station 22 or a master station 24, module 72 can be coupled to base module 74, if desired. The display screen of module 72 is approximately a 10 inch display screen in some embodiments and therefore is larger than the LCD screen used in, for example, the COMLINX® system.

Each of the communications links 30, 34, 36, 44, 46, 50, 54, 60, 62, 66 shown diagrammatically by lines or arrows in FIG. 1 may include wired links and/or wireless links and/or combinations thereof, along with associated connectors. For example, with regard to links 44 between beds 42 and bed connector units 40, known cables having 37-pin connectors (or similar connectors) may provide these links 44. Alternatively or additionally, some of links 44 may be wireless links, in which case, the respective beds 42 and units 40 have appropriate wireless transmitter and wireless receiver circuitry, which may be in the form of a wireless transceiver. Such wireless communication between beds 42 and units 40 is discussed, for example, in U.S. Pat. No. 7,319,386 and in U.S. Patent Application Publication No. 2007/0210917 A1, both of which are hereby incorporated herein by this reference.

While this disclosure contemplates that the data formatting for the data transmitted over any of links 30, 34, 36, 44, 46, 50, 54, 60, 62, 66, 68, 70 may be according to any suitable data formatting protocol, in one embodiment, the data formatting protocol is according to the protocol discussed in detail in the "Project NCM II, Interface Design Specification, NPD05514" document which is attached to U.S. Provisional Patent Application No. 61/066,877 as Appendix 1 and which is considered part of the written description of that provisional patent application and of this patent application via the incorporation by reference previously made in this application of U.S. Provisional Patent Application No. 61/066,877. In general, the protocol described in Appendix 1 of U.S. Provisional Patent Application No. 61/066,877 uses extensible markup language (XML) strings to transfer data. This protocol is sometimes referred to as the Palmetto Protocol and is sometimes referred to as the XML protocol herein and in some of the documents in the Appendices of the written description of U.S. Provisional Patent Application No. 61/066,877. It is also contemplated that the communication protocol for links 30, 34, 36, 44, 46, 50, 54, 60, 62, 66 may be according to any suitable protocol such as the TCP/IP protocol, the RS-232 protocol, the RS-422 protocol, the RS-423 protocol, or the RS-485 protocol, or similar such protocols, and such as wireless protocols including any of the IEEE 802.11$_x$ protocols (where x represents the various revision levels a, b, c, d, e, g and so forth of the 802.11 protocol), the Bluetooth protocol, the Zigbee protocol, or similar such wireless communication protocols.

In one embodiment, links 44, 46, 54, 62, which are the communications links associated with a patient room that communicate between devices in the patient room and the I/O circuit board of dome light assembly 28, are according to the RS-485 protocol, whereas links 34, 36, 68, 70, which are the links to and from PoE switch 32, are according to the TCP/IP protocol. The devices that communicate over these various links are configured and programmed appropriately for the required RS-485 or TCP/IP protocol, as the case may be.

It should be noted that, in one contemplated embodiment, link 30 comprises a coupler that couples to a PoE port of the respective I/O circuit 27 such that communications over link 30 are transmitted according to the TCP/IP protocol and I/O circuit 27 provides feed through of any data, including communication data such as voice data, communicated between station 22 and PoE switch 32. Because stations 22 communicate according to the TCP/IP protocol, staff stations 22 are coupleable to PoE switch 32 without the use of an intervening I/O circuit 27, if desired. As to the various devices coupled to I/O circuit 27 other than station 22, the circuitry of I/O circuit 27 operates to convert the data from these various devices according to their device-specific communication protocols (e.g., serial links to stations 122, 222; locating and tracking receiver 56 room bus protocol; bed connector 40 room bus protocol; and serial to dome light protocol) into the TCP/IP protocol for subsequent transmission to the PoE switch and ultimately to the master station 24 and beyond, if desired.

According to this disclosure, system 20 is scaleable such that basic, intermediate, and advanced nurse call systems can be created depending upon the particular requirements of a particular healthcare facility. The graphical audio stations 22 discussed herein are associated with an advanced nurse call system and are referred to in several of the documents of the Appendices of U.S. Provisional Patent Application No. 61/066,877, which are considered part of this written description via incorporation by reference, as an advanced graphical audio station (AGAS) and are referred to in the documents of the Appendices of U.S. Provisional Patent Application No. 61/145,306, which is also considered part of this written description via incorporation by reference, as a Graphical Room Station 10 (GRS-10). A 42-page electric circuit schematic illustrating one possible electric circuit implementation of one embodiment of an advanced graphical audio station (AGAS) 22 according to this disclosure is shown in FIG. 11 of U.S. Provisional Patent Application No. 61/066,877. In one embodiment, audio graphical station 22 is an IBM part no. 43T2058 station.

A graphical audio station 122, shown in FIG. 1, provides mid-range or intermediate functionality and includes a smaller graphical display screen 124 than the display screen of stations 22. This type of intermediate station 122 is referred to in the documents of the Appendices of U.S. Provisional Patent Application No. 61/066,877 as a graphical audio station (GAS) and in the documents of the Appendices of U.S. Provisional Patent Application No. 61/145,306 as a Graphical Room Station 5 (GRS-5). FIGS. 13 and 14 of U.S. Provisional Patent Application No. 61/066,877 cooperate to provide an electric circuit schematic illustrating one possible electric circuit implementation of one embodiment of graphical audio station (GAS) 122. Graphical audio station 122 in one embodiment comprises IBM part nos. 43T2071 and 43T2067.

A standard audio station 222, shown in FIG. 2 and referred to in the documents of the Appendices of U.S. Provisional Patent Application No. 61/066,877 as a standard audio station (SAS) and referred to in the Appendices of U.S. Provisional Patent Application No. 61/145,306 as Standard Room Station (SRS) has no graphical display screen. A 20-page electric circuit schematic illustrating one possible electric circuit implementation of one embodiment of standard audio station 222 is shown in FIG. 16 of U.S. Provisional Patent Application No. 61/066,877. Graphical audio station 222 in one embodiment comprises IBM part no. 43T2082. Additional details of stations 22, 24, 122, 222 are provided in a U.S. Provisional Patent Application No. 61/066,882 which was filed Feb. 22, 2008, which is titled "User Station for Healthcare Communication System," and which is already incorporated by reference herein.

Standard audio stations 222 are a low cost offering that provides call cancel, call placement, reception for signals from badges 58, and voice communication functionality. As mentioned already, stations 222 do not have a graphical display. Stations 222 connect to the I/O circuit board of assembly 28 via an RS-485 connection 30. Stations 222 can be configured as a patient station, staff station, or visitor station. As indicated in FIG. 2, beds 42 may couple to stations 222 via an audio station bed connector (ASBC) 224. Also, pillow speaker units 226 and/or a call switch 52 (e.g., a call cord in some instances) may couple to station 222, such as by coupling to a connector 225 included as part of station 222. It is contemplated that bed connector 224 can be integrated into station 22 and thus, in FIG. 2, reference numeral 224 is used to denote such an integrated connector 224 of station 222 as well as the separate bed connector block 224. In the FIG. 2 example, however, bed 42 is coupled to a Silver Plate 228 which is, in turn, coupled to the associated I/O board 27. The term "Silver" refers to the general color of the plate, not its material.

While FIG. 2 shows one block representative of I/O circuit 27 and shows two separate dome light assemblies 28 linked to it via unnumbered double-headed arrows, it should be appreciated that in some embodiments each assembly 28 has its own I/O circuit 27 as discussed previously. However, this need not be the case in all instances and therefore, having I/O circuits 27 located elsewhere in system 20 is within the scope of this disclosure. As further shown in FIG. 2, bed connector 40 is coupled to I/O circuit board 27 via an RS-485 communications link 230. FIG. 2 also shows station 22 coupled to I/O circuit 27 via link 30, PoE switch coupled to I/O circuit 27 via link 34, nurse call switch 52 coupled to I/O circuit 27 via link 54, a wireless receiver 56 coupled to I/O circuit 27 via link 62, and PoE switch 32 coupled to master station 24 via link 36. A staff station 22 is also shown in FIG. 2 in communication with master station 22 via link 70. While link 70 is shown directly between master console 24 and staff console 22, this is intended to be representative of a "logical link" to indicate that staff stations 22 communicate all received commands to the master station 24 and receive information about all other devices, such as patient stations 22, of the nursing unit from master station 24. Thus, staff stations 22 communicate with master station 24 via PoE switch 32.

Intermediate level audio stations 122 are a mid range offering that provides all of the functionality that a standard audio station 222 provides. In addition, stations 122 have small touch screen displays 124 that allow for monitoring calls, monitoring other types of alerts, view the location of staff, call located staff, change bed status (e.g., clean or dirty status), enable and disable nurse calls and alerts for a location or for a nursing unit. Unlike station 222, station 122 runs a Linux operating system (OS) that drives the graphical display and responds to user interaction. The content for display 124 of station 122 is controlled by the associated I/O circuit board 27 and by advanced services which are resident on other computer devices of system 20 as will be further discussed below. For base functionality, the I/O circuit controls the display of station 122 by sending XML strings to station 122. The circuitry of station 122 interprets those strings and displays a corresponding user interface (UI). If an advanced functionality is requested by station 122, the I/O circuit forwards the request for the advanced service(s) and the computer device of system 20 having the advanced service(s) replies back with the content in the appropriately formatted XML string.

In the illustrative example, advanced level audio stations 22, 24 provide all of the functionality of stations 122 except stations 22 couple to bed connectors 40, 224 via I/O circuits and not directly. However, in other embodiments contemplated herein, either of connectors 40, 224 may be integrated into station 22 or connected thereto in a manner similar to which they are integrated or connected in stations 122, 222 as described above. Stations 22, 24 also run a Linux OS, but it is written in C# programming code and executed under Mono, an open source implementation of the .NET framework maintained by Novell. This permits some code sharing between base and advanced systems as discussed in more detail below, and in the Appendices of U.S. Provisional Patent Application No. 61/066,877 which are already incorporated by reference herein.

In broad general terms, it is the stations 22, 24 which are configured to communicate with various other computer devices, such as servers, included in the Ethernet of a healthcare facilities' system 20 and it is this additional communication capability that distinguishes these devices as advanced graphical audio stations. According to this disclosure, the components of system 20 which cooperate to provide a healthcare facility with a nurse call system are referred to collectively as a "base nurse call system." Thus, stations 22, 122, 222 and I/O circuit 27, dome light assemblies 28, and any of the equipment described above that is capable of providing a nurse call signal, as well as the associated master station 24 and PoE switch 32 along with any of the communication links interconnecting these components, are among the components which comprise a "base nurse call system" according to this disclosure. Staff stations 22, if present, are also considered to comprise part of the base nurse call system.

If voice communication capability among stations 22, 24, 122, 222 is to be a function of the nurse call system, then a Voice over Internet Protocol (VoIP) sever 250 is also included in the base nurse call system and is coupled to PoE switch 32 via a TCP/IP communications link 252 as shown in FIG. 2. Server 250 facilitates communication between which ever of stations 22, 24, 122, 222 are present in the system 20. Server 250 is configured to translate system operations and communications to the corresponding messages that then control endpoint devices, such as stations 22, 122, consoles 24, or room input/output circuits 27. As such, server 250 includes a soft telephony switch and other associated components. Server 250 may also provide integration with the hospital telecommunications structure (e.g., PBX or other voice communication system), although some other server may do so as well as is discussed below. In the illustrated embodiment, server 250 is a Windows server running 3CX. The components of the base nurse call system of illustrative system 20 are compliant with Underwriter's Laboratories 1069 standard according to this disclosure. This is not to imply that these components may not also be compliant with other standards relating to nurse call systems or relating to some other aspect of these devices.

According to this disclosure, stations 22, 24 also permit users to perform functions associated with an "advanced services system." The software code, such as applets or plug-ins, that provides stations 22 with these advanced functions may be communicated from various servers, or similar such computer devices discussed below, to stations 22 via stations 24, PoE switch 32, I/O boards 27, and the associated links 30, 34, 36. Thus, stations 22, 24 are dependent upon some devices that are not part of the base nurse call system, but instead are part of the advanced services system, to provide the advanced functionality to stations 22, 24. However, if these other devices are inoperable or communications with such devices of the advanced services system cannot be established or is otherwise faulty, the base nurse call system functionality is still able to operate. Thus, functionally, the base nurse call system is isolated from the advanced services system from a hardware standpoint and from a software standpoint.

Figure 3:
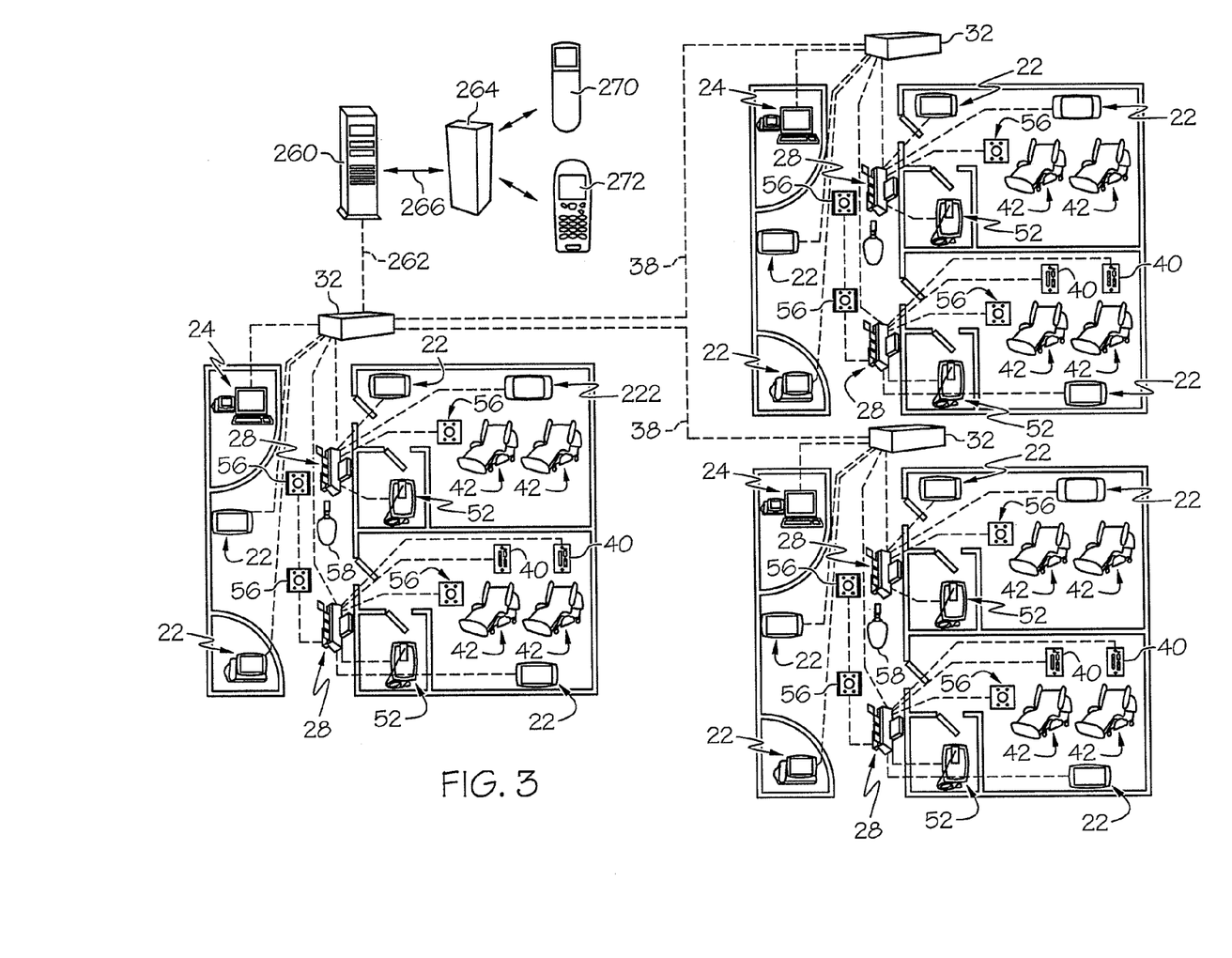
FIG. 3 is block diagram showing nurse call systems of various nursing units of a healthcare facility coupled to each other and coupled to other computer devices of the healthcare facility.

System 20 includes an enterprise server 260 which is included as part of the advanced services system as shown in FIGS. 1-3. Server 260 links to the nurse call portion of system 20 to provide advanced services thereto. A communication link 262 exists between server 260 and master station 24 via an appropriate switch device, such as a PoE switch 32 or other type of switch. Multiple master stations 24 may connect to server 260 via a switch 32 as shown in FIG. 3. As shown in FIG. 1, a private branch exchange (PBX) 264 may be coupled to server 260 via a VoIP communications link 266 to permit two-way voice calls to be placed over the public switched telephone network (PSTN) 268 to telephones outside the healthcare facility from graphical audio stations 22, 24, 122 by appropriate use of user inputs of user interfaces displayed on stations 22, 24, 122 as part of an associated advanced service. Two-way voice calls may be made similarly via server 260 and PBX 264 to wireless voice communication devices, such as a wireless communication badge 270 (e.g., a Vocera™ badge) or a wireless hand set 272, shown in FIG. 3, in response to appropriate use of the user interfaces of stations 22, 24, 122. Text messages may be sent to devices both inside and outside the healthcare facility via these same communications links in response to use of the user interfaces of stations 22, 24, 122. PSTN 268 is intended to represent, diagrammatically, a variety of telecommunication devices, including analog and digital devices, fixed telephones and mobile or cellular devices, personal data assistants (PDAs), pagers and the like.

As shown in FIG. 2, a non-exhaustive list of examples of other computer devices, each of which is optional according to this disclosure, that communicate via appropriate communications links with enterprise server 260 and therefore, with associated master stations 24 of one or more nurse call systems, include a database server 280; one or more third party servers 282; a first wireless communications server 284 for managing communications to and from wireless telecommunications devices; a second wireless communications server 286 for handling communications to and from other devices such as wireless badges for locating and tracking of staff members; a user authentication server 288 for managing user accounts, passwords, and user authorization; a workflow server 290, which facilitates integration with workflow software systems; a hospital administrative client 292 for conducting administrative tasks relating to patients and staff, such as adding patients and assigning staff to patients; and a status or reports server 294 for managing displays and reports of calls and notifications for one or more locations in the facility. An electronic status board 296 may also be coupled to server 260 as shown diagrammatically in FIG. 2. Status board 296 is operable to display locations within the facility and current information about them, such as active calls, bed status information, staff located in the healthcare facility, and staff assigned to the location.

While the term "server" is used herein, it will be understood by those skilled in the art that the functionality represented or performed by devices referred to as "severs" may comprise and be performed by any suitable computer device having software programs or services that may be resident and/or executable by any computer, device or equipment in the system or more than one computer, device or equipment in the network. Thus, there term "server" is intended to broadly encompass any computer device that is capable of performing the mentioned functions.

In the illustrated embodiment, server 284 is configured to provide communication and configuration for wireless devices using Emergin Wireless Office; server 286 is configured to provide communication and configuration for wireless Vocera devices; server 290 is configured to interface with or be included as part of a Hill-Rom® NaviCare™ system to receive and process task assignment and completion information. Plug-ins or applets or similar such software code may be resident on any of servers 260, 282, 284, 286, 288, 290, 292, 294, for example, and be retrieved by stations 22, 24 via server 260 as part of the "advanced services system" functionality. The software to display a particular user interface associated with an advanced service on a particular station 22, 24 which is operated by a user in a manner resulting in the request of the advance service may be executed on a device other than the one that requested it. For example, such advance service software may be executed by the circuitry of a master station 24 or I/O circuit 27, but yet the resulting user interface is display on one of stations 22. Additional details of the advanced services functionality are shown and described in the "Code Blue Advanced System Software, Architectural Design Specification, NPD05503" document attached to U.S. Provisional Patent Application No. 61/066,877 as Appendix 2 and is considered part of the written description of this patent application via incorporation by referenced of U.S. Provisional Patent Application No. 61/066,877. Further details of system 20 and its functionality are also provided in this same U.S. Provisional Patent Application No. 61/066,877.

Figure 4:
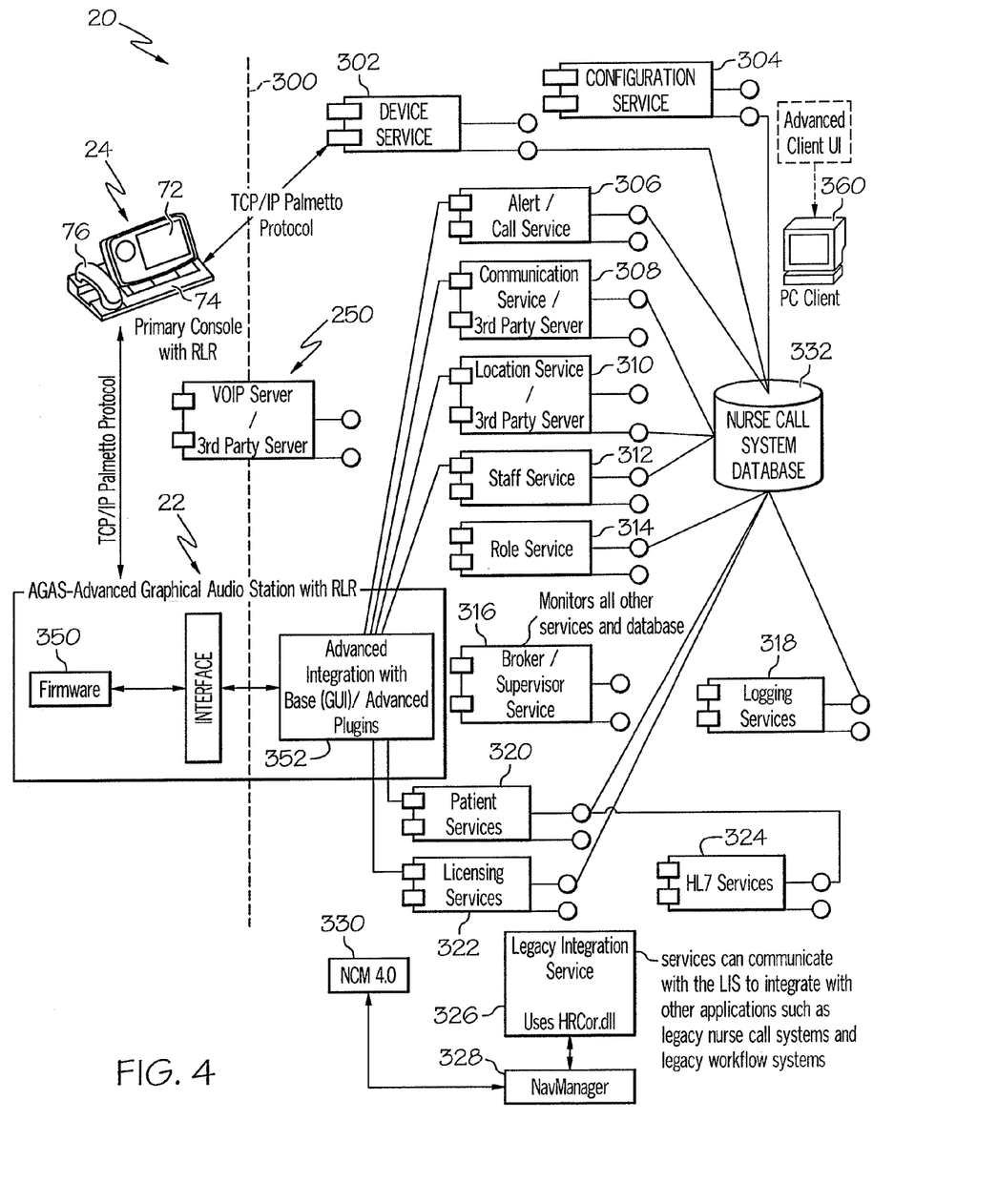
FIG. 4 is a block diagram showing a number of software modules associated with an advanced services system of the healthcare communication system, the software modules having being communicatively coupled to a master station and to other graphical audio stations of the nurse call system so that software plug-ins are distributable to the master a station and to the other graphical audio stations to provide additional functionality to these devices.

Referring now to FIG. 4, logical interconnections between various software modules of the advanced services system and the base nurse call system are illustrated diagrammatically. Software modules are sometimes referred to herein as just modules. A dashed line 300 represents the logical division between the base nurse call system, which is to the left of dashed line 300, and the advanced services system, which is to the right of dashed line 300. As mentioned above, plug-ins or applets or similar such software code or modules may be resident on any of servers 260, 282, 284, 286, 288, 290, 292, 294, for example, and be retrieved by stations 22, 24 via server 260 as part of the "advanced services system" functionality. Server 260 includes a device service module 302 which provides system 20 with a device service.

The primary console 24 is configured to communicate with a specific IP address and port which are associated with the device service. The device service accepts any incoming connections from one or more primary consoles 24 and monitors the consoles 24 to determine if any advanced service functionality is to be delivered to a particular console 24, possibly for subsequent distribution by console 24 to other devices, such as stations 22, 122 and circuit 27, for example. The various activities occurring in the base nurse call system are communicated by consoles 24 to the device service which operates to relay relevant data to any other advanced service or any other computer device which have subscribed to receive such data or to which the device service publishes such data.

In the illustrative example, the advanced services system includes a configuration service module 304, an alert/call service module 306, a communication service module 308, a location service module 310, a staff service module 312, a roll services module 314, a broker/supervisor service module 316, a logging service module 318, a patient service module 320, a licensing service module 322, an HL7 service module 324, and a legacy integration service module 326. Legacy integration service module 326 provides connectivity to existing nurse call systems, such as the COMLINX® system, which is represented in FIG. 4 by NCM 4.0 block 330. Illustrative, module 326 communicates bidirectionally with the illustrative legacy nurse call system 330 via a NavManager 328. The various modules 302, 304, 306, 308, 310, 312, 314, 316, 318, 320, 322, 324, 326 post data to and retrieve data from a data base 332. Database 332 may reside on one or more separate database servers or may be included on server 260 or may be included in a database server cluster, for example.

As mentioned above, device service module 302 is resident on server 260. However, it is within the scope of this disclosure for any one or more of service modules 302, 304, 306, 308, 310, 312, 314, 316, 318, 320, 322, 324, 326 to be resident on any one or more of servers 260, 282, 284, 286, 288, 290, 292, 294. In one embodiment, however, all of service modules 302, 304, 306, 308, 310, 312, 314, 316, 318, 320, 322, 324, 326 are resident on server 260. The listed service modules and/or other service modules may also be resident on VoIP server 250 in other embodiments.

If one of the advanced services needs to transmit commands or information to a device of the base nurse call system, for example, if the advanced service needs to communicate to primary console 24 an alert condition occurring in some other portion of system 20 or the advanced system needs to command the I/O circuit 27 to reset, device service 302 sends to the primary console 24 the data or command through a TCP/IP socket connection of the primary console 24 using the XML over TCP/IP protocol discussed above and in the Appendices of U.S. Provisional Patent Application No. 61/066,918 which is already incorporated by reference herein.

This disclosure contemplates a second line of communication to devices of the base nurse call system, which second line of communication is through a defined interface. The base application running on stations 22, 24 is written in C# using Mono on Linux as mentioned previously. Advanced features are enabled on stations 22, 24 by pushing advanced plug-ins down to stations 22, 24 and having them dynamically loaded in separate application domains when needed. The description below of how plug-ins operate on one of stations 22 is applicable to other stations 22, 24 as well, and also to stations 122 in some embodiments.

A logical representation of this second line of communication is illustrated in FIG. 4 with regard to graphical audio station 22. As shown in FIG. 4, firmware 350 is provided in station 22 on an embedded computing platform. The firmware 350 provides station 22 with its core nurse call functionality. Station 22 also has advanced services system integration software 352 that is compatible with the server computer platform of the advanced services system and that receives the various software plug-ins from the advanced services system. It should be appreciated that the various lines in FIG. 4 interconnecting integration software 352 with advanced services 306, 308, 310, 312, 320, 322 are logical connections, not hardware connections.

Station 22 has an interface 354 between firmware 350 and integration software. Interface 354 is a control interface and, in the illustrative embodiment, is not intended to transfer data. Data transfer through interface 354 may occur in other embodiments, however. Interface 354 provides the ability of station 22 to load and unload one or more plug-ins, start and stop the functionality of the plug-ins, and show and hide the plug-in's user interface, if the plug-in has one associated with it.

When a new device, such as one of stations 22, 24 or I/O circuit 27, is added to the system, server 260 pushes one or more software plug-ins, as appropriate, from one or more of advanced service modules 302, 304, 306, 308, 310, 312, 314, 316, 318, 320, 322, 324, 326 in response to server 260 becoming aware of the new device. The one or more software plug-ins are installed and become operational when launched, such as when a user first uses an associated advanced service on the device. Future updates and upgrades of the plug-ins pushed to the new device are also sent to the new device automatically.

According to this disclosure, system 20 includes a hospital administrative client computer 360 as shown in FIG. 4. Computer 360 is used, for example, for patient and staff administrative tasks, such as adding patients, discharging patients, assigning staff members to patients and/or locations, changing device assignment for staff, and so forth. Computer 360 is a so-called "rich client" deployable and updated via a central server. Multiple computers 360 may be included in system 20 and have any or all of these functions.

Computer 360 may also be used to distribute software upgrades and updates throughout system 20, including to devices of the base nurse call system. The software upgrades and updates are distributable all at once to the multiple devices using computer 360. This eliminates the need to load software upgrades and updates on individual computer devices of the base nurse call system. Microsoft ClickOnce application software is an example of software that computer 360 may use to implement this manner of software upgrades and updates.

It should be appreciated that, as to the base nurse call system components, the software upgrades and updates distributed by computer 360 relate only to the advanced functionality of the base nurse call system and not the core nurse call functionality of the base nurse call system. That is, the software updates and upgrades do not change any of the firmware 350 of the embedded computer platforms of stations 22, 24 or other devices of the base nurse call system, such as circuit 27. By isolating the core nurse call functionality from the advanced services functionality of stations 22, 24 in this way, recertification for compliance with the UL-1069 standard is not needed when any of the advanced services are upgraded or updated or additional advanced services added. Thus, regulated functionality of the base nurse call system is isolated on a software basis and/or a hardware basis from the advanced services that are run on some of the devices of the base nurse call system.

The architecture of system 20 allows a user to have access to both the core nurse call functionality and other optional features that are available seamlessly via the embedded computing platform of stations 22, 24, and stations 122 in some embodiments. By use of software plug-ins to accomplish this, stable software that is stored locally is combined with the optional software of the plug-ins, which is applied to the embedded platform as needed. For example, a portion of a user interface on the graphical display screens of stations 22, 24, 122, are generated with local software, whereas other user interfaces, or portions thereof, are generated by the software plug-ins but this is generally unknown and undetected by the user.

In one embodiment, server 260 is a Windows-based server platform capable of running .NET 3.0 in order to support Windows Communications Foundation (WCF), a service architecture framework provided by Microsoft. Advanced service modules 302, 304, 306, 308, 310, 312, 314, 316, 318, 320, 322, 324, 326 are implemented in WCF and communicate using deployment-time configured protocols. In the case in which all of service modules 302, 304, 306, 308, 310, 312, 314, 316, 318, 320, 322, 324, 326 are running on the same machine, such as server 260, each service communicates to the others using Named Pipes which is an efficient means of communication and supports state machine deployment. In other instances, service modules 302, 304, 306, 308, 310, 312, 314, 316, 318, 320, 322, 324, 326 are configured to communicate via a binary TCP/IP protocol, using Microsoft Message Queuing (MSMQ) to provide substantially guaranteed delivery, and Hypertext Transfer Protocol (HTTP) when providing compatibility to Mono and other third party integrations. Each service modules 302, 304, 306, 308, 310, 312, 314, 316, 318, 320, 322, 324, 326 may be configured to communicate over more than one binding in order to support simultaneous usage from legacy systems as well as base nurse call system disclosed herein. Additional details of the service modules 302, 304, 306, 308, 310, 312, 314, 316, 318, 320, 322, 324, 326 are provided in the document attached as Appendix 2 to U.S. Patent Application No. 61/066,918 which is already incorporated by reference herein.

System 20 is configured in a tiered architecture arrangement to incorporate several levels of fault tolerance, redundancy, and self monitoring to lessen the impact of component failures on users of the system. System 20 is tiered at several levels to achieve this fault tolerance. For example, the room gateway (e.g., I/O circuit) has sufficient computing power and functionality to allow a patient, caregiver, or monitoring device to initiate an alert even if there is a major fault in a portion of the system 20 not associated with the particular patient room. This aspect of system 20 may be referred to as room survivability. Another level of the tiered architecture arrangement is that the master nurse station console 24 has sufficient computing power and functionality to run an entire nursing unit with all the core nurse call system functionality, even if server 260 has a major failure. This aspect of system 20 may be referred to as nursing unit survivability.

At the enterprise level of system 20, which includes, but is not limited to, the devices associated with the advanced services system, there are many hardware and software mechanisms included throughout the system that allow some or all of the system 20 to remain functional despite the occurrence of a variety of faults. For example, any one or more of servers 250, 260, 282, 284, 286, 288, 290, 292, 294 may be equipped with at least one of Redundant Arrays of Independent Disks or Drives (RAID), redundant power supplies, or clustering failover capability. Broker service module 316 operates to monitor the health of the other service modules 302, 304, 306, 308, 310, 312, 314, 318, 320, 322, 324, 326 and is operable to repair or restart faulty services, in some instances.

As mentioned above, system 20 comprises a software architecture that incorporates distributed Publish and Subscribe (PubSup) data communication technology. This allows many services and applications to easily communicate and share data with each other. The PubSub data communication technology allows this data sharing between software services and applications on the same computing platform or between many computing platforms across a network. Each service or application, such as one or more of service modules 302, 304, 306, 308, 310, 312, 314, 316, 318, 320, 322, 324, 326, has the ability to publish or make available its data to other services or applications (e.g., subscribers) that have a use for the data. As the data changes, the subscribers are automatically updated.

Stations 22, 24, and stations 122 in some embodiments, as well as I/O circuit 27 each include auto-discovery technology, such as software, that allows these computer devices to discover their network connectivity settings, software modules, and other system responsibilities when first installed in system 20. Each of these computer devices are configured with the auto-discovery technology at the time of manufacture. When a device is installed, the auto-discovery software of the device operates to automatically seek and initiate contact with a device manager. The device manager, such as server 260, will then communicate appropriate network settings, transfer the required software modules, and/or assign other responsibilities to the newly installed device. That newly installed device is then operational on system 20 once this information from the device manager is received.

According to this disclosure, in some embodiments, system 20 incorporates software-based or hardware-based Session Initiation Protocol (SIP) voice over internet protocol (VoIP) technology to separate the set up and tear down of voice calls between SIP enabled voice endpoint devices. This is accomplished having a separate VoIP private branch exchange (PBX), such as PBX 264 (e.g., hard-ware based) or servers 250 284, 286 (software-based), that has connectivity to the rest of system 20 and/or to PSTN 268. System 20 also incorporates a VoIP room gateway, such as I/O circuit 27, which can distribute voice communications to multiple voice terminals or VoIP voice endpoints installed in patient rooms and hallways.

As is apparent from the discussion above, some of the improvements realized by system 20 over prior art systems include the following improvements. The distributed architecture retains and preserves the most critical functionality at the local user level should a failure occur in system 20 outside that local area, which lessens system wide impact due to single points of failure. Distributing software updates and upgrades from administration computer device 360 greatly reduces the time required to perform updates and upgrades to numerous devices and lessens the chance that devices are not updated due to human error. Computer 360 permits a user to easily and quickly install software applications on numerous devices. Also, software maintenance is simplified by having some updates and upgrades distributed automatically when a particular application is launched. Use of software plug-ins allows the core nurse call functionality software to be developed, built, and tested separate from the optional software. This lessens the chance of the core software being adversely affected by changes to the optional software. It also allows the core software to remain more stable though product life cycle and reduce the number of regulatory submissions. It should be appreciated that various system embodiments according to this disclosure may not be configured to have all of the improvements mentioned above in this paragraph or even any of them.

Additional improvements realized by system 20 over prior art systems include the following improvements. The fault tolerant, tiered architecture arrangement of system 20 increases reliability by reducing single points of failure in the system. It also allows a technician to perform maintenance on the system while impacting few or no other users. The PubSub technology allows communication and sharing to occur more efficiently and makes software development easier and faster because individual developers are able to focus on their particular software application or service. The auto-discovery technology eases installation and greatly reduces installation and repair times, as well as eliminating the need for the installation technician to connect to each device, one at a time, to configure network settings and install software. Having a separate SIP VoIP PBX allows the healthcare facility to select from a variety of compliant PBX's on the market or to use one the facility already possesses for their other voice systems. The SIP VoIP PBX also isolates less critical voice features from the core nurse call alert notification features. The flexibility to use either a software-based or hardware-based SIP VoIP PBX gives healthcare facilities the option to install this functionality on existing servers or to use a high reliability hardware appliance to support voice features of the system. Use of the VoIP room gateway gives the healthcare facility the flexibility to select lower cost voice terminals with limited functionality or higher cost VoIP voice endpoints with more functionality. It should be appreciated that various system embodiments according to this disclosure may not be configured to have all of the improvements mentioned above in this paragraph or even any of them.

Although certain illustrative embodiments have been described in detail above, variations and modifications exist within the scope and spirit of this disclosure as described and as defined in the following claims.

The invention claimed is:

1. A healthcare communication system comprising:
a first plurality of computer devices operable as a nurse call system, the first plurality of computer devices having core nurse call functionality residing on an embedded computing platform, at least one of the first plurality of computer devices having a graphical display screen, and
a second plurality of computer devices operable to provide the first plurality of computer devices with additional functionality via at least one software plug-in that is transmitted from at least one of the second plurality of computer devices to at least one of the first plurality of computer devices.

2. The healthcare communication system of claim 1, wherein the graphical display screen has a user interface that, when used by a user, results in the at least one software plug-in being transmitted to at least one of the first plurality of computer devices.

3. The healthcare communication system of claim 2, wherein the at least one of the first plurality of computer devices to which the at least one software plug-in is transmitted comprises at least one of a master station, a patient room station located in a patient room of the healthcare facility, an input/output (I/O) circuit that is coupled to the patient station, or a staff station located in a staff work area of the healthcare facility.

4. The healthcare communication system of claim 1, wherein the at least one software plug-in is operable to change the user interface of the graphical display screen to a different user interface.

5. The healthcare communication system of claim 1, wherein the second plurality of software devices are configured such that the at least one software plug-in is transmitted to the at least one of the first plurality of computer devices on an as needed basis as dictated by use of the at least one of the first plurality of computer devices.

6. The healthcare communication system of claim 1, wherein the second plurality of software devices are configured such that the at least one software plug-in is transmitted to some or all of the first plurality of computer devices in response to use of at least one of the second plurality of computer devices.

7. The healthcare communications system of claim 1, wherein software upgrades or updates installed on at least one of the second plurality of computer devices are distributed automatically to at least some of the first plurality of computer devices.

8. The healthcare communications system of claim 7, wherein the software upgrades or updates are also distributed automatically to at least one other computer device of the second plurality of computer devices.

9. The healthcare communications system of claim 1, wherein, in response to a new computer device being added to the first plurality of computer devices, at least one of the second plurality of computer devices automatically transmits at least one software plug-in to the new computer device.

10. The healthcare communications system of claim 1, wherein the core nurse call functionality comprises functionality regulated by a regulations entity and the additional functionality comprises non-regulated functionality.

11. The healthcare communications system of claim 1, wherein at least one of the first plurality of computer devices and the second plurality of computer devices incorporates Publish and Subscribe (PubSub) data communication technology.

12. The healthcare communication system of claim 1, wherein at least one of the first plurality of computer devices is communicatively coupled to a hospital bed and receives bed status data from the hospital bed.

13. The healthcare communication system of claim 1, wherein at least one computer device of the first plurality of computer devices has auto-discovery software that is operable, in response to installation of the at least on computer device in the nurse call system, to detect network connectivity and to initiate communications with a device manager.

14. The healthcare communication system of claim 13, wherein the device manager is operable to provide software modules and/or network settings to the at least one computer device of the first plurality of computer devices.

15. The healthcare communication system of claim 1, further comprising least one additional computer device that is coupled to at least one of the computer devices of the first plurality or second plurality of computer devices and that incorporates Session Initiation Protocol (SIP) voice over Internet protocol (VoIP) technology to separate the setting up and tearing down of voice calls between SIP enabled voice endpoint devices.

16. The healthcare communication system of claim 15, wherein the at least one additional computer device comprises a VoIP private branch exchange (PBX).

17. The healthcare communication system of claim 1, wherein at least one of the first computer devices comprises a VoIP room gateway that is operable to distribute communication data to multiple voice terminals or VoIP voice endpoints installed in patient rooms and hallways.

18. The healthcare communication system of claim 1, wherein the first plurality of computer devices are interconnected in a tiered architecture arrangement to provide fault isolation among the tiers so that faults occurring in computer devices of one tier don't affect the operability of computer devices in other tiers.

19. The healthcare communication system of claim 18, wherein at least one of the tiers comprises a subset of the first plurality of computer devices that is associated with a patient room.

20. The healthcare communication system of claim 18, wherein at least one of the tiers comprises a subset of the first plurality of computer devices that is associated with a nursing unit having a plurality of patient rooms.

\* \* \* \* \*